(12) United States Patent
Wang et al.

(10) Patent No.: US 10,510,141 B2
(45) Date of Patent: Dec. 17, 2019

(54) METHOD AND APPARATUS FOR DETERMINING ILLUMINATION INTENSITY FOR INSPECTION, AND METHOD AND APPARATUS FOR OPTICAL INSPECTION

(71) Applicants: BOE TECHNOLOGY GROUP CO., LTD., Beijing (CN); CHONGQING BOE OPTOELECTRONICS TECHNOLOGY CO., LTD., Chongqing (CN)

(72) Inventors: Xu Wang, Beijing (CN); Chaoqiang Liu, Beijing (CN); Zhengdong Xi, Beijing (CN); Yang Liu, Beijing (CN)

(73) Assignees: BOE Technology Group Co., Ltd., Beijing (CN); Chongqing BOE Optoelectronics Technology Co., Ltd., Chongqing (CN)

( * ) Notice: Subject to any disclaimer, the term of this patent is extended or adjusted under 35 U.S.C. 154(b) by 130 days.

(21) Appl. No.: 15/552,126

(22) PCT Filed: Mar. 16, 2017

(86) PCT No.: PCT/CN2017/076916
§ 371 (c)(1),
(2) Date: Aug. 18, 2017

(87) PCT Pub. No.: WO2017/202114
PCT Pub. Date: Nov. 30, 2017

(65) Prior Publication Data
US 2018/0158185 A1 Jun. 7, 2018

(30) Foreign Application Priority Data
May 23, 2016 (CN) .......................... 2016 1 0342920

(51) Int. Cl.
*G06K 9/00* (2006.01)
*G06T 7/00* (2017.01)
(Continued)

(52) U.S. Cl.
CPC ........... *G06T 7/0004* (2013.01); *G01N 21/00* (2013.01); *H04N 5/23229* (2013.01);
(Continued)

(58) Field of Classification Search
CPC ...... G01N 21/8806; G06T 2207/10152; G06T 5/50; H04N 5/2354; H04N 5/2251; H04N 5/2256; G06K 9/4661
See application file for complete search history.

(56) References Cited

U.S. PATENT DOCUMENTS

| | | | |
|---|---|---|---|
| 6,627,863 B2* | 9/2003 | Wasserman | G01J 1/32 250/205 |
| 2004/0178351 A1* | 9/2004 | Kim | G01N 21/8806 250/372 |

(Continued)

FOREIGN PATENT DOCUMENTS

| | | |
|---|---|---|
| CN | 101419176 | 4/2009 |
| CN | 101556380 | 10/2009 |

(Continued)

OTHER PUBLICATIONS

International Search Report from corresponding PCT Application No. PCT/CN2017/076916 dated Jun. 20, 2017 (5 pages).
(Continued)

*Primary Examiner* — Li Liu
(74) *Attorney, Agent, or Firm* — Harness, Dickey & Pierce, P.L.C.

(57) ABSTRACT

The present disclosure relates to a method and apparatus for determining an illumination intensity for inspection, and an method and apparatus optical inspection. The method for determining an illumination intensity for inspection comprises: acquiring images of a sample to be inspected taken by each of at least one imaging element at a plurality of illumination intensities; calculating, for each imaging ele-
(Continued)

ment, a gray standard deviation of each of the images acquired at the plurality of illumination intensities; and determining the illumination intensity of each imaging element for inspection according to the gray standard deviation. The inspection accuracy may be improved by using the illumination intensity determined by the method provided in the present disclosure to inspect an object to be inspected.

14 Claims, 8 Drawing Sheets

(51) Int. Cl.
    *G01N 21/00*     (2006.01)
    *H04N 5/232*     (2006.01)
(52) U.S. Cl.
    CPC ............... *G06T 2207/30121* (2013.01); *G06T 2207/30141* (2013.01); *G06T 2207/30148* (2013.01)

(56) References Cited

U.S. PATENT DOCUMENTS

2007/0258070 A1* 11/2007 Fujiwara ............ G03F 7/70341
    355/53
2011/0103679 A1* 5/2011 Campbell .......... G01B 11/0608
    382/152
2013/0033620 A1* 2/2013 Polidor ................ H04N 5/2354
    348/240.3
2016/0148073 A1* 5/2016 Uffenkamp ........... G06T 3/4038
    348/148
2017/0262968 A1* 9/2017 Stoppe .................... G06T 5/003

FOREIGN PATENT DOCUMENTS

| CN | 101676695 | 3/2010 |
| CN | 103905731 | 7/2014 |
| CN | 105911724 | 8/2016 |
| JP | 2007043439 | 2/2007 |
| JP | 2014211411 | 11/2014 |

OTHER PUBLICATIONS

Written Opinion from corresponding PCT Application No. PCT/CN2017/076916 dated Jun. 20, 2017 (5 pages).

Office Action from corresponding Chinese Application No. 201610342920.0 dated Aug. 25, 2017 (6 pages).

* cited by examiner

METHOD AND APPARATUS FOR DETERMINING ILLUMINATION INTENSITY FOR INSPECTION, AND METHOD AND APPARATUS FOR OPTICAL INSPECTION

CROSS-REFERENCE TO RELATED APPLICATION

This application claims priority and benefit of Chinese Patent Application No. 201610342920.0, filed on May 23, 2016, the entire content of which is incorporated by reference herein.

FIELD

Embodiments of the present disclosure relate to the field of automated optical inspection, and more particularly to a method and apparatus for determining an illumination intensity for inspection, and a method and apparatus for optical inspection.

BACKGROUND

AOI (Automated Optical Inspection) is an effective inspection method for industrial automation. It uses machine vision as the standard inspection technology. It is widely used in LCD/TFT, transistor and PCB industrial processes, and can be extended to security systems in people's livelihood. The automated optical inspection is a common representative method in industrial processes, which utilizes an optical manner to obtain the surface state of an object to be inspected and inspects defects such as a foreign object or an abnormal pattern through image processing. Because it is non-contact inspection, semi-finished products can be inspected in intermediate processes. When an automated inspection is performed, the machine automatically scans an inspection object through a camera, collects an image thereof, compares the solder joints tested to qualified parameters in a database, finds out, after image processing, defects on the object, and displays/denotes the defects through a display or an automated sign for maintaining by the maintenance personnel.

BRIEF SUMMARY

The embodiments of the present disclosure provide a method and apparatus for determining an illumination intensity for inspection, and a method and apparatus for optical inspection, which may obtain the illumination intensity for inspection, so as to improve the accuracy of inspection when inspecting an object using the obtained illumination intensity.

In an embodiment described herein, there is provided a method for determining an illumination intensity for inspection which comprises:

acquiring images of a sample to be inspected taken by each of at least one imaging element at a plurality of illumination intensities;

calculating, for each imaging element, a gray standard deviation of each of the images acquired at the plurality of illumination intensities; and determining the illumination intensity of each imaging element for inspection according to the gray standard deviation.

In an embodiment, the at least one imaging element is configured to take images of different regions of the sample to be inspected.

In an embodiment, determining the illumination intensity of each imaging element for inspection according to the gray standard deviation comprises:

normalizing the gray standard deviations for each imaging element;

determining a preferred illumination intensity range of each imaging element according to the normalized gray standard deviations and corresponding relationship between the normalized gray standard deviations and the plurality of illumination intensities;

acquiring an intersection of the preferred illumination intensity ranges of the at least one imaging element; and determining the illumination intensity of each imaging element for inspection according to the intersection.

In an embodiment, determining the preferred illumination intensity range for each imaging element comprises:

determining a range between the illumination intensities corresponding to the normalized gray standard deviation that is equal to a predetermined value as the preferred illumination intensity range of each imaging element.

In an embodiment, acquiring the intersection of the preferred illumination intensity ranges of the at least one imaging element comprises:

determining whether there is the intersection among the preferred illumination intensity ranges of the individual imaging elements, and if so, acquiring the intersection;

otherwise, gradually reducing the predetermined value until there is the intersection among the acquired preferred illumination intensity ranges of the individual imaging elements and acquiring the intersection.

In an embodiment, the predetermined value is no less than 0.8.

In an embodiment, determining the illumination intensity of each imaging element for inspection according to the intersection comprises:

determining an intermediate value in the intersection as the illumination intensity of each imaging element for inspection.

In an embodiment, determining the illumination intensity of each imaging element for inspection according to the gray standard deviations comprises:

determining, for each imaging element, the illumination intensity corresponding to a largest gray standard deviation among the gray standard deviations as the illumination intensity of each imaging element for inspection.

In an embodiment, the sample to be inspected is a color film substrate, a thin film transistor array substrate, or a printed circuit board for a liquid crystal display.

In another embodiment, there is provided a method for optical inspection which comprises:

selecting at least one object to be inspected from a plurality of objects to be inspected as a sample to be inspected;

determining the illumination intensity of each of the at least one imaging element for inspection according to the method described in any of the preceding embodiments, by using the sample to be inspected; and optically inspecting the plurality of objects to be inspected by using the determined illumination intensity.

In yet another embodiment, there is provided an apparatus for determining an illumination intensity for inspection, which comprises:

at least one imaging element configured for taking an image of a sample to be inspected;

an image acquisition unit configured for acquiring images of the sample to be inspected taken by each imaging element at a plurality of illumination intensities;

a calculation unit configured for calculating, for each imaging element, a gray standard deviation of each of images acquired at the plurality of illumination intensities; and an illumination intensity determination unit configured for determining the illumination intensity of each imaging element for inspection according to the gray standard deviation.

In an embodiment, the at least one imaging element is configured to take images of different regions of the sample to be inspected.

In an embodiment, the illumination intensity determination unit comprises:

a normalization unit configured for normalizing the gray standard deviation for each imaging element;

a preferred illumination intensity range determination unit configured for determining a preferred illumination intensity range of each imaging element according to the normalized gray standard deviations and corresponding relationship between the normalized gray standard deviations and the plurality of illumination intensities;

an intersection acquisition unit configured for acquiring an intersection of the preferred illumination intensity ranges of the at least one imaging element; and an illumination intensity determination sub-unit configured for determining the illumination intensity of each imaging element for inspection according to the intersection.

In an embodiment, the preferred illumination intensity range determination unit is further configured for:

determining a range between the illumination intensities corresponding to the normalized gray standard deviation that is equal to a predetermined value as the preferred illumination intensity range of each imaging element.

In an embodiment, the intersection acquisition unit is further configured for:

determining whether there is an intersection among the preferred illumination intensity ranges of the individual imaging elements, and if so, acquiring the intersection among the preferred illumination intensity ranges of the at least one imaging element; otherwise, gradually reducing the predetermined value until there is an intersection among the acquired preferred illumination intensity ranges of the individual imaging elements.

In an embodiment, the predetermined value is no less than 0.8.

In an embodiment, the illumination intensity determination sub-unit is further configured for:

determining an intermediate value in the intersection as the illumination intensity of each imaging element for inspection.

In an embodiment, the illumination intensity determination unit is further configured for:

determining, for each imaging element, the illumination intensity corresponding to a largest gray standard deviation among the gray standard deviations as the illumination intensity of each imaging element for inspection.

In yet another embodiment, there is provided an apparatus for optical inspection, which comprises the apparatus configured for determining the illumination intensity for inspection described in any of the embodiments.

In the exemplary embodiment described herein, the illumination intensity for inspection is determined from the gray standard deviation of the image. The greater the gray standard deviation of the image, the more detailed information that the image contains, and the more helpful to the inspection of defects of the sample to be inspected. Therefore, the accuracy of inspection may be improved by using the illumination intensity determined by the method described in the embodiments herein to inspect the object to be inspected.

Further aspects and areas of applicability will become apparent from the description provided herein. It should be understood that various aspects of this application may be implemented individually or in combination with one or more other aspects. It should also be understood that the description and specific examples herein are intended for purposes of illustration only and are not intended to limit the scope of the present application.

BRIEF DESCRIPTION OF THE DRAWINGS

The drawings described herein are for illustrative purposes only of selected embodiments and not all possible implementations, and are not intended to limit the scope of the present application.

In the drawings.

Corresponding reference numerals indicate corresponding parts or features throughout the several views of the drawings.

DETAILED DESCRIPTION

Exemplary embodiments will now be described more fully with reference to the accompanying drawings.

During the automated optical inspection, the used illumination intensity has great influence on the accuracy of inspection. In the related art, people first inspect a sample to be inspected at a different illumination intensity, and determines whether the illumination intensity is the optimum illumination intensity according to the number of inspected defects. The greater the number of inspected defects, the more accurate the result of inspection at this illumination intensity, and then people may use this illumination intensity for bulk inspection of the object to be inspected.

Figure 1A:
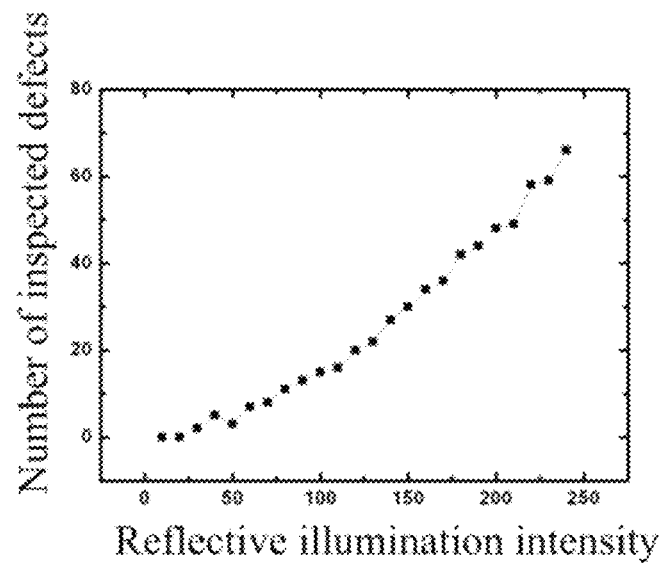
FIGS. 1a and 1b respectively show the curve of correlation between the number of defects and the illumination intensity during reflective illumination and the curve of correlation between the number of defects and the illumination intensity during transmissive illumination.
Figure 1B:
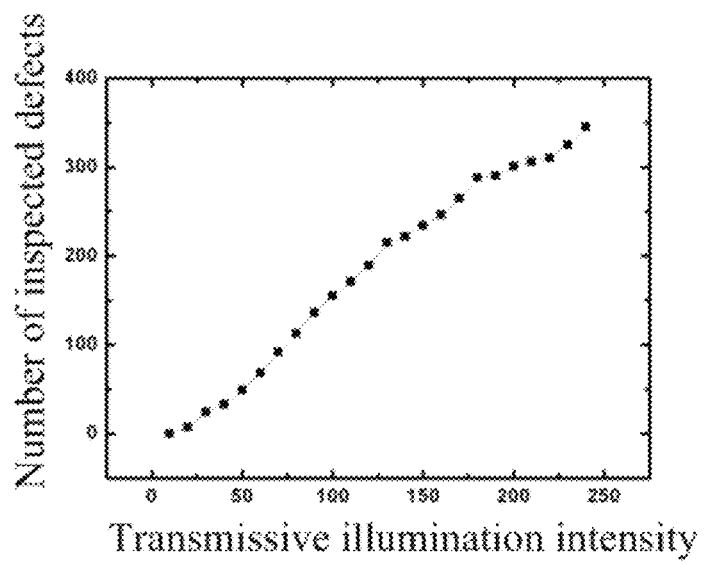
Figure 2A:
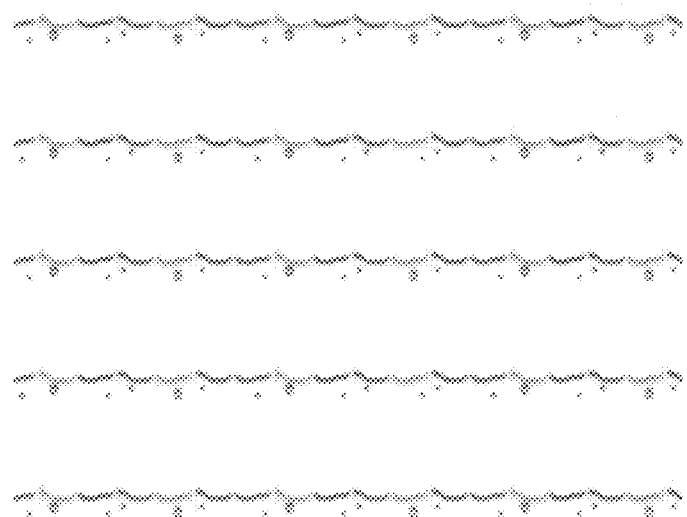
FIGS. 2a and 2b respectively show images of a sample to be inspected taken by using a relatively strong illumination intensity and a relatively weak illumination intensity through reflective illumination.
Figure 2B:
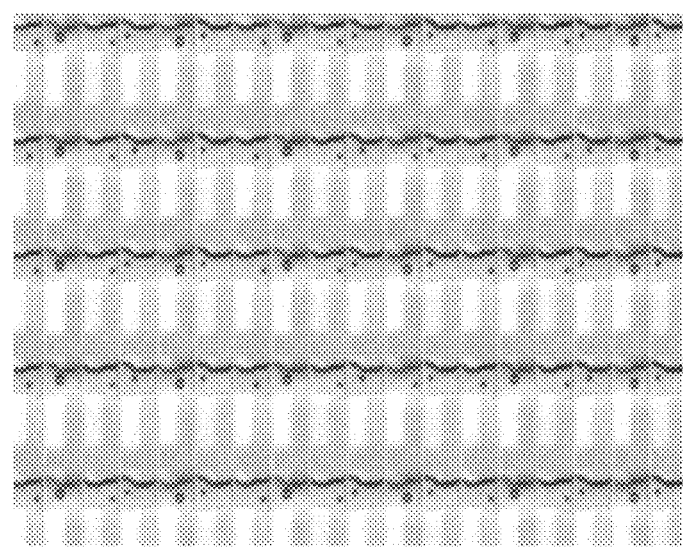
Figure 3A:
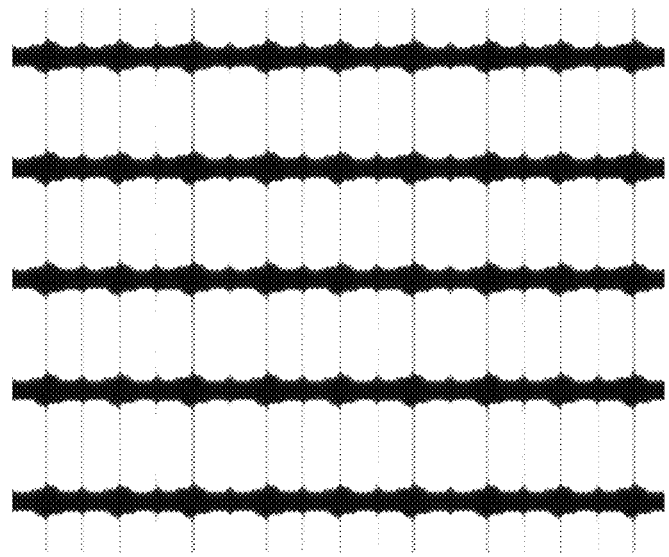
FIGS. 3a and 3b respectively show images of a sample to be inspected taken by using a relatively strong illumination intensity and a relatively weak illumination intensity through transmissive illumination.
Figure 3B:
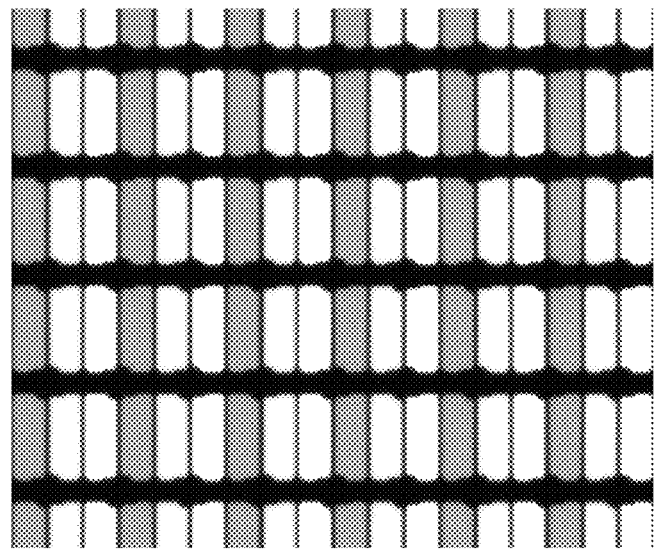

FIGS. 1a and 1b respectively show the curve of correlation between the number of defects and the illumination intensity during reflective illumination and the curve of correlation between the number of defects and the illumination intensity during transmissive illumination. As shown in FIGS. 1a and 1b, regardless of reflective illumination or transmissive illumination, the stronger the illumination intensity, the more the number of inspected defects, whereby the use of strong illumination may improve the inspection accuracy theoretically. However, in fact, in a case that the illumination intensity is strong, the image details are liable to be lost, and the inspected defects may contain components of falsely inspected. FIGS. 2a and 2b respectively show images of a sample to be inspected taken by using a relatively strong illumination intensity and a relatively weak illumination intensity through reflective illumination. FIGS. 3a and 3b respectively show images of a sample to be inspected taken by using a relatively strong illumination intensity and a relatively weak illumination intensity through transmissive illumination. As can be seen from FIGS. 2a, 2b, 3a and 3b, regardless of reflective illumination or transmissive illumination, in a case that the illumination intensity is strong, the image details are seriously lost, which may cause a false inspection. On the other hand, in a case that the illumination intensity is weak, the image details are more obvious, but it is impossible to determine a better illumination intensity since there is no peak in the case that the illumination intensity is weak, as shown in FIGS. 1a and 1b.

The method for determining an illumination intensity for inspection provided in the embodiments of the present disclosure may inspect defects as many as possible while reducing the probability of false inspection and thus improving the inspection accuracy.

Figure 4:
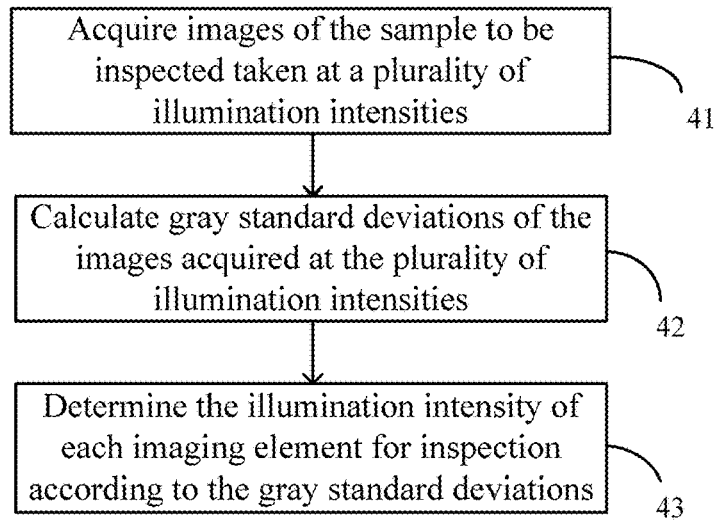
FIG. 4 schematically shows a flow diagram of a method for determining an illumination intensity for inspection according to an embodiment.

It is to be noted that, in the embodiments described herein, one or more objects to be inspected may be selected from a plurality of objects to be inspected as the sample to be inspected, and the illumination intensity for inspection is determined by implementing the method for determining the illumination intensity provided in the embodiments of the present invention. Using the determined illumination intensity can implement an inspection of a single object to be inspected or of a batch of objects to be inspected. For example, when it is desired to inspect a protective layer on a color film substrate of a liquid crystal display, an color film substrate having a protective layer finished thereon may be selected as a sample to be inspected to determine an illumination intensity for inspection, and then the determined illumination intensity may be used for bulk inspection of protective layers on the color film substrates. FIG. 4 schematically shows a flow diagram of a method for determining an illumination intensity for inspection according to an embodiment.

Referring to FIG. 4, a method for determining an illumination intensity for inspection comprises the steps:

image acquisition step 41: acquiring images of different regions of the sample to be inspected taken by each imaging element at a plurality of illumination intensities;

gray standard deviation calculation step 42: calculating, for each imaging element, a gray standard deviation of each of the images acquired at the plurality of illumination intensities; and illumination intensity determination step 43: determining the illumination intensity of each imaging element for inspection according to the gray standard deviations.

In the embodiments described herein, at least one imaging element may take images of the object/sample to be inspected under illumination at a plurality of illumination intensities. If there are a plurality of imaging elements, the plurality of imaging elements are configured to take images of different regions of the object/sample to be inspected, respectively. For example, if there are five imaging elements, the five imaging elements are responsible for taking images of five different regions of the object/sample to be inspected, respectively.

Each of these foregoing steps will be described in detail with reference to the accompanying drawings. For purpose of description, the method for determining the illumination intensity for inspection is described by taking a plurality of imaging elements as an example in the embodiments disclosed herein.

At the image acquisition step 41, each of the plurality of imaging elements takes images of the sample to be inspected under illumination of the plurality of different illumination intensities to acquire a plurality of images of the sample to be inspected. As described above, each imaging element is responsible for taking images of different regions of the sample to be inspected. In an embodiment, the imaging element may be configured to take images of the sample to be inspected through a reflective illumination mode, and may also be configured to take images of the sample to be inspected through a transmissive illumination mode.

In an alternative embodiment, the illumination intensity may be set to be 0-255 levels to correspond to 0-255 gray levels of the image. The plurality of illumination intensities may be selected from the 0-255 levels. For example, for each imaging element, the illumination intensity may be gradually increased from 10 to 250 at a pitch of 10 to sequentially take an image of the sample to be inspected, and thus each imaging element may take 25 pictures.

At the gray standard deviation calculation step 42, a larger gray standard deviation of the image indicates more detail information comprised in the image, and is more favorable to the inspection of the defects of the sample to be inspected. Therefore, in the embodiment described herein, the gray standard deviation of the image may be used as the basis for determining whether the illumination intensity is optimum.

At the time of operation, the gray standard deviation of each image may be calculated by the following equation:

$$\delta = \sqrt{\frac{1}{MN-1} \sum_{x=1}^{M} \sum_{y=1}^{N} [I(x, y) - I_0]^2}$$

Where $\delta$ is the standard deviation, M and N represent the number of pixels in the x and y directions, respectively, I (x, y) represents the gray value of a certain point on the image, and $I_0$ represents the average gray value of the image.

In the illumination intensity determination step 43, for each imaging element, the illumination intensity corresponding to the maximum gradation standard deviation can be determined as the illumination intensity of each imaging element for inspection. With the illumination intensity determined by this method, the optimum illumination intensity of each imaging element may be obtained. However, since the hardware performance of each imaging element may not be exactly the same, the optimum illumination intensity of each imaging element may be different. If an optical inspection is performed on an object to be inspected, it is necessary to set respective illumination intensity for each imaging element.

Figure 5:
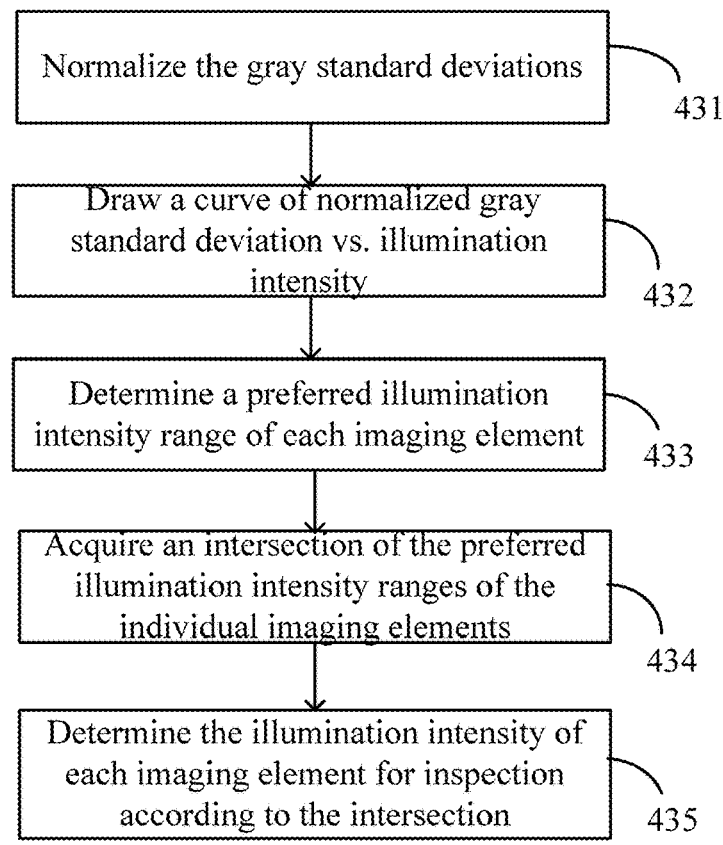
FIG. 5 schematically shows a flow diagram of an exemplary method for determining a illumination intensity for inspection based on a gray standard deviation.

In another exemplary embodiment, referring to FIG. 5, the illumination intensity for inspection may also be determined by the following steps:

normalization step 431: normalizing the gray standard deviations for each imaging element;

σ-I curve drawing step 432: for each imaging element, drawing a curve of normalized gray standard deviation vs. illumination intensity (σ-I curve);

preferred illumination intensity range determination step 433: determining a preferred illumination intensity range of each imaging element according to corresponding relationship between the normalized gray standard deviations and the plurality of illumination intensities;

intersection acquisition step 434: acquiring an intersection of the preferred illumination intensity ranges of the individual imaging elements; and step 435: determining the illumination intensity of each imaging element for inspection according to the intersection acquired in step 434.

With the illumination intensity determined by the exemplary method shown in FIG. 5, each imaging element may use the same illumination intensity for illumination when a batch inspection is performed on the objects to be inspected, without the need to set a different illumination intensity for each imaging element, which is simple in operation, and conducive to the unity of inspection standards.

at the normalization step 431, the normalization can be performed by the following equation:

$$\sigma = \frac{\delta}{\delta_{max}}$$

Where, σ is the normalized gray standard deviation of the image, δ is the gray standard deviation of the image, and $\delta_{max}$ is the maximum gray standard deviation corresponding to a single imaging element. It is to be understood that the gray standard deviations can also be normalized by other methods, for example normalizing with a logarithmic function or an arctangent function.

Figure 6:
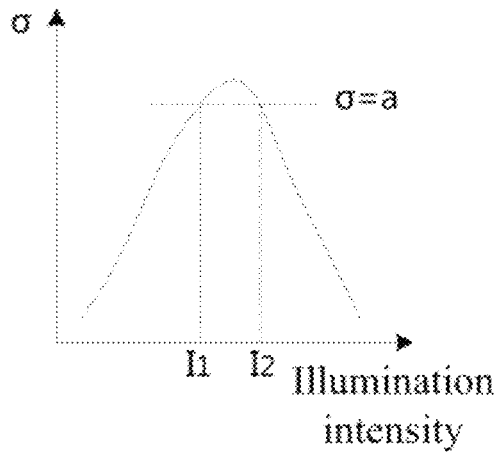
FIG. 6 schematically shows a σ-I curve for a single imaging element.

At the σ-I curve drawing step 432, a σ-I curve can be drawn for each imaging element. FIG. 6 schematically shows a σ-I curve of a single imaging element. As can be seen from FIG. 6, the drawn σ-I curve has a peak, so that the preferred illumination intensity for inspection can be determined according to the curve.

At the preferred illumination intensity range determination step 433, the preferred illumination intensity range of each imaging element may be acquired from the σ-I curve drawn in step 432. In an exemplary embodiment, a range between the illumination intensities corresponding to the normalized gray standard deviation that is equal to a predetermined value may be determined as the preferred illumination intensity range of each imaging element. For each imaging element, the predetermined value may be set as a, where 0<a≤1. As shown in FIG. 6, σ=a (a≠1) corresponds to two illumination intensities $I_1$ and $I_2$, and the illumination intensity range between $I_1$ and $I_2$ (including $I_1$ and $I_2$) is determined as the preferred illumination intensity range of the imaging element. In a particular embodiment, when a=1, it only corresponds to one illumination intensity, and it may be considered that there is only one element in the preferred illumination intensity range.

At the intersection acquisition step 434, the intersection of these preferred illumination intensity ranges are obtained according to the preferred illumination intensity ranges of the individual imaging elements acquired in the preferred illumination intensity determination step 433.

During specific operations, exemplarily, the intersection may be acquired by the following steps:

i) setting a=1, determining whether the corresponding illumination intensities of the individual imaging elements are the same when a=1, and if so, using the illumination intensity as the illumination intensity for inspection; otherwise, executing step ii)

ii) reducing the value of a;

iii) determining whether a is greater than a predetermined threshold b, where 0<b≤1, and if so, executing step IV); otherwise, debugging the hardware of the apparatus for optical inspection; and IV) acquiring the preferred illumination intensity range corresponding to σ=a, determining whether there is an intersection among the preferred illumination intensity ranges of the individual imaging elements, and if so, acquiring the intersection among the preferred illumination intensity ranges of the individual imaging elements; otherwise, returning to the step ii).

Generally, the individual imaging elements of the apparatus for optical inspection have the same or similar hardware configuration. If the value of a is reduced to sufficiently small, e.g., less than a predetermined threshold b, and there is still no intersection among the preferred illumination intensities of the individual imaging elements, it means that the hardware of the apparatus for optical inspection may be problematic, whereby it is necessary to debug the hardware. After debugging, the intersection may be acquired again by the above method so as to acquire the illumination intensity for inspection according to the intersection.

In an embodiment, the predetermined threshold is set to be 0.8.

At step 435, an intermediate value in the intersection of the preferred illumination intensity ranges of the respective imaging elements are determined as the illumination intensities of the individual imaging elements for inspection so that each imaging element uses the same illumination to take the images, thereby facilitating operations and the unity of inspection standards.

In an exemplary embodiment, the sample to be inspected may be a color film substrate, a thin film transistor (TFT) array substrate, or a printed circuit board (PCB) for a liquid crystal display.

In the production process of a product, for each forming process of the product, the illumination intensity for inspection may be determined using the method provided in the embodiments described herein, and then the illumination intensity may be used to inspect whether there are defects in the elements formed by the process, so as to repair the defects in time. For example, if the object to be inspected is a color film substrate of a display, in the process of manufacturing the color film substrate, after a black matrix is formed, the method provided in the embodiments described herein may be used to determine the illumination intensity for inspecting the black matrix, and then the determined illumination intensity may be used to inspect whether there are defects on the black matrix of the color film substrate so as to repair the defects of the black matrix in time; after a color filter is formed on the color film substrate, the method provided in the embodiments described in the present invention may be used to determine an illumination intensity for inspecting the color filter, and then the determined illumination intensity may be used to inspect whether there are defects in the color filter so as to repair the defects of the color filter in time. According to the same method, a defect inspection may be performed after each element (e.g., protective layer and columnar spacer, etc.) is formed sequentially so as to repair the defects in time when they exist.

In the exemplary embodiments described herein, the illumination intensity for inspection may be determined according to the gray standard deviation of the image. As described above, the greater the gray standard deviation of the image, the more detailed information that the image contains, and the more helpful to the inspection of defects of the sample to be inspected. Therefore, the accuracy of inspection may be improved by using the illumination intensity determined by the method described in the embodiments herein to inspect the object to be inspected.

Figure 7:
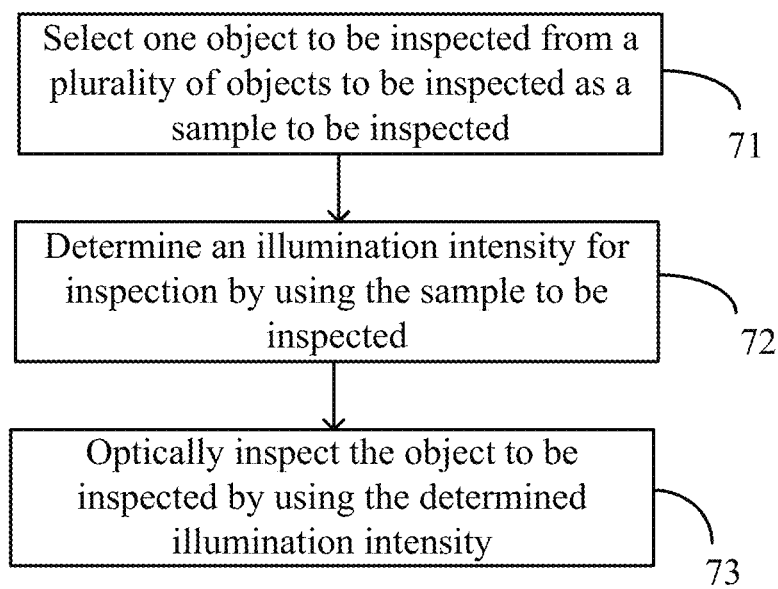
FIG. 7 schematically shows a flow diagram of a method for optical inspection according to an embodiment.

FIG. 7 schematically shows a flow diagram of a method for optical inspection according to an embodiment. As shown in FIG. 7, the illumination intensity inspection method comprises:

Step 71 of selecting at least one object to be inspected from a plurality of objects to be inspected as a sample to be inspected;

Step 72 of determining an illumination intensity for inspection by using the sample to be inspected; and Step 73 of optically inspecting the objects to be inspected by using the determined illumination intensity.

At step 72, in order to inspect the objects to be inspected, it is possible to first select one of the objects to be inspected as the sample to be inspected and then apply the method shown in FIGS. 4 to 6 to the sample to be inspected to determine the illumination intensity for inspection, so as to perform bulk optical inspection of the objects to be inspected by using the determined illumination intensity.

At step 72, since the illumination intensity for inspection may be determined by using the same method as that described in the above embodiments and shown in FIGS. 4 to 6, the explanations and descriptions of the method for determining the illumination intensity for inspection and the advantages thereof in the above-described embodiments with reference to FIGS. 4 to 6, may also be applicable to the present embodiment.

As shown above, since the object to be inspected is inspected using the illumination intensity determined by the method provided in the embodiments described herein, the inspection accuracy may be improved.

The flow charts depicted herein are just one example. There may be many variations to these charts or the steps described therein without departing from the spirit of the disclosure. For instance, the steps may be performed in a differing order or steps may be added, deleted or modified. For example, the normalization step 431 may be omitted and a curve of the gray standard deviation vs. illumination intensity may be drawn directly; and the curve of the gray standard deviation vs. illumination intensity may also be replaced with a corresponding table of the gray standard deviation vs. illumination intensity, all of which are considered a part of the claimed aspect.

Figure 8:
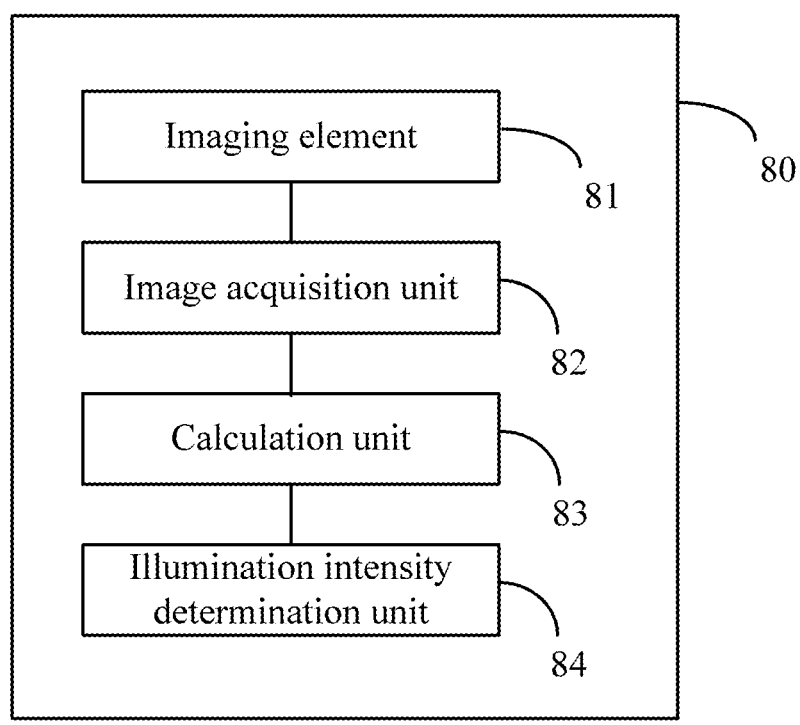
FIG. 8 schematically shows a block diagram of an apparatus for determining an illumination intensity for inspection according to an embodiment.

FIG. 8 schematically shows a block diagram of an apparatus for determining an illumination intensity for inspection according to an embodiment. As shown in FIG. 8, the apparatus 80 for determining the illumination intensity for inspection comprises at least one imaging element 81, an image acquisition unit 82, a calculation unit 83, and an illumination intensity determination unit 84.

The at least one imaging element 81 may be configured for taking an image of a sample to be inspected, and in particular, the at least one imaging element may be configured to take images of different regions of the sample to be inspected, respectively.

The image acquisition unit 82 may be configured for acquiring images of the sample to be inspected taken by each imaging element at a plurality of illumination intensities.

The calculation unit 83 may be configured for calculating a gray standard deviation of each of images acquired at a plurality of illumination intensities for each imaging element.

The illumination intensity determination unit 84 may be configured for determining the illumination intensity of each imaging element for inspection according to the gradation standard deviations.

In an exemplary embodiment, the illumination intensity unit 84 may further comprise a normalization unit, a preferred illumination intensity range determination unit, an intersection acquisition unit, and an illumination intensity determination sub-unit, wherein the normalization unit is configured for normalizing the gray standard deviations of each imaging element; the preferred illumination intensity range determination unit is configured for determining a preferred illumination intensity range of each imaging element according to the normalized gray standard deviations and a corresponding relationship between the normalized gray standard deviations and the plurality of illumination intensities; the intersection acquisition unit is configured for acquiring an intersection of the preferred illumination intensity ranges of the at least one imaging element; and the illumination intensity determination subunit is configured for determining, according to the intersections, the illumination intensity of each imaging element for inspection.

In an exemplary embodiment, the preferred illumination intensity range determination unit may be further configured for determining a range of the illumination intensities corresponding to the normalized gray standard deviation that is equal to a predetermined value as the preferred illumination intensity range of each imaging element.

In an exemplary embodiment, the intersection acquisition unit may be further configured for determining whether there is an intersection among the preferred illumination intensity ranges of the individual imaging elements, and if so, acquiring the intersection among the preferred illumination intensity ranges of the at least one imaging element; otherwise, gradually reducing the predetermined value until there is an intersection among the acquired preferred illumination intensity ranges of the imaging elements.

In an exemplary embodiment, the predetermined value is no less than 0.8.

In an exemplary embodiment, the illumination intensity determination sub-unit may be further configured for determining an intermediate value in the intersection as the illumination intensity of each imaging element for inspection.

Alternatively, the illumination intensity determination unit 84 may be further configured for determining, for each imaging element, the illumination intensity corresponding to the largest gray standard deviation among the gray standard deviations as the illumination intensity of each imaging element for inspection.

The apparatus for determining the illumination intensity for inspection provided in the embodiments described herein may determine the illumination intensity for inspection. Specifically, the method for determining the illumination intensity for inspection described in the embodiments abovementioned and shown in FIGS. 4-6 may be used to determine the illumination intensity for inspection. Therefore, the explanations and descriptions of the method for determining the illumination intensity for inspection and the advantages thereof in the above-described embodiments with reference to FIGS. 4 to 6, are also applicable to the present embodiment.

In a further embodiment, there is provided an apparatus for optical inspection configured for performing an automated optical inspection on an object to be inspected. The apparatus for optical inspection comprises the apparatus for determining the illumination intensity for inspection as provided by preceding embodiments.

Since the apparatus for optical inspection comprises the apparatus for determining the illumination intensity for inspection as provided by preceding embodiments, the explanations and descriptions of the apparatus for determining the illumination intensity for inspection in the preceding embodiments, are also applicable to the present embodiment.

It shall be appreciated that, the units or modules such as the image acquisition unit, the calculation unit, the illumination intensity determination unit, the normalization unit, the preferred illumination intensity range determination unit, the intersection acquisition unit, and the illumination intensity determination sub-unit described herein may be implemented as a combination of a processor and a memory, wherein the processor executes a program stored in the memory to implement the functionality of the corresponding units or modules. The units or modules describes herein may also be completely implemented by hardware, including but not limited to Application Specific Integrated Circuits (ASICs), Field Programmable Gate Arrays (FPGAs).

Example

To make the purpose, technical solutions and advantages of the present disclosure more clear, the method for determining an illumination intensity for inspection provided in the embodiments of the present disclosure will be described below in detail with reference to a specific example.

In this example, a protective layer on a color film substrate is inspected by an apparatus for automated optical inspection having 19 reflective cameras, to determine an illumination intensity for inspection. Further, the determined illumination intensity may be used for batch inspection of the protective layer on the color film substrate.

Figure 9:
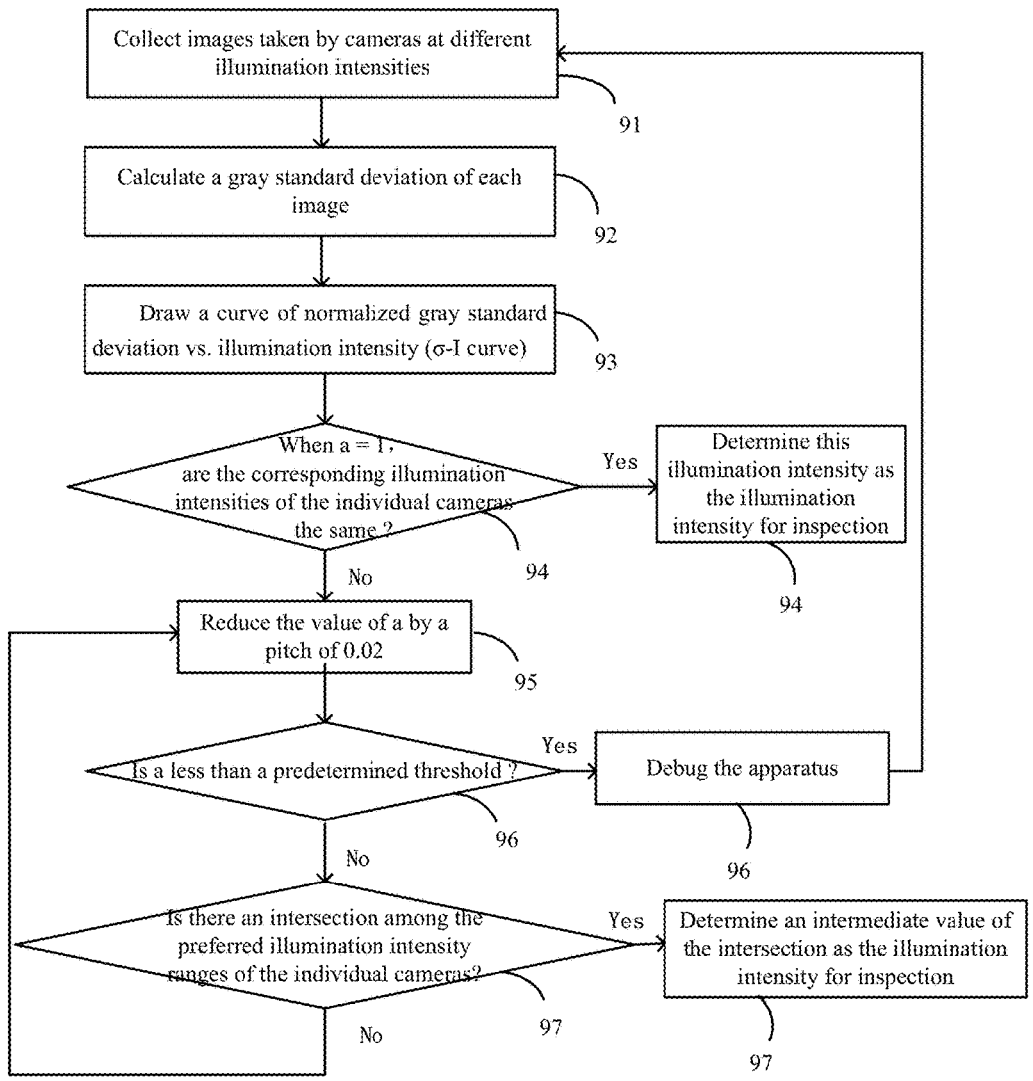
FIG. 9 schematically shows a flow diagram of a method for determining an illumination intensity for inspection in an embodiment.
Figure 10:
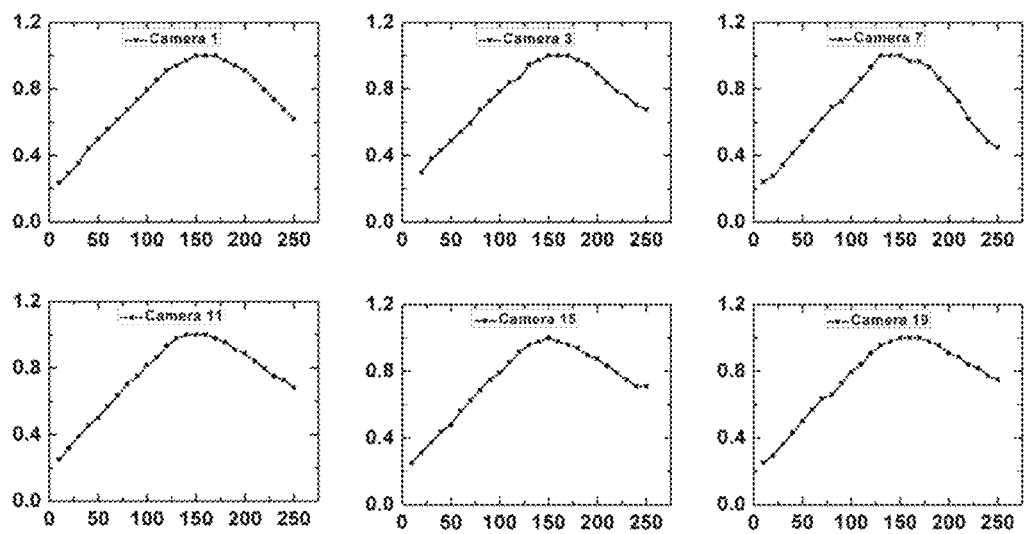
FIG. 10 shows the σ-I curve corresponding to the camera 1/3/7/11/15/19 in the embodiment shown in FIG. 9.

FIG. 9 schematically shows a flow diagram of a method for determining an illumination intensity for inspection in the example. In this example, the illumination intensity is set to gradually increase from 10 to 250 at a pitch of 10, in which case each camera can take 25 images at 25 different illumination intensities. As shown in FIG. 9, the method for determining the illumination intensity for inspection comprises the following steps:

step 91: collect images of a sample to be inspected taken by the 19 cameras at different reflective illumination intensities;

step 92: for each camera, calculating a gray standard deviation of each image by image processing software;

step 93: for each camera, drawing a curve of gray standard deviation vs. illumination intensity;

At the step 93, the gray scale standard deviation may be normalized, in which case the curve of the normalized gray standard deviation vs. illumination intensity ($\sigma$-I curve) may be drawn. FIG. 10 shows the $\sigma$-I curves corresponding to the cameras 1, 3, 7, 11, 15, and 19 respectively. In FIG. 10, the vertical ordinate represents the normalized gray standard deviation and the abscissa represents the illumination intensity.

step 94: setting a=1, determining whether the corresponding illumination intensities of individual cameras are the same when $\sigma$=a, and if so, determining the illumination intensity as the illumination intensity for inspection; otherwise, executing step 95;

step 95: reducing the value of a by a pitch of 0.02;

step 96: determining whether a is less than a predetermined threshold (e.g., 0.8), if so, debugging the apparatus, and then returning to step 91; if not, executing step 97;

step 97: acquiring an illumination intensity range between the two illumination intensities I1 and I2 corresponding to $\sigma$=a as a preferred illumination intensity range, and determining whether there is an intersection among the acquired preferred illumination intensity ranges of individual cameras; if so, determining an intermediate value of the intersection as the illumination intensity for inspection; otherwise, returning to step 95.

At step 96, if a is less than a predetermined threshold, and no intersection is found, it means that there may be a problem with the apparatus, which may be debugged, such as by adjusting the focus position of the camera lens, adjusting the camera gain, and so on.

In this example, the illumination intensity ranges of the individual cameras have an intersection [148, 168] when $\sigma$=a=0.94, therefore the preferred illumination intensity range of the apparatus for automated optical inspection is [148, 168], and the intermediate value of the preferred illumination intensity range 158 is set as the illumination intensity for inspection. Using the illumination intensity to perform an automated optical inspection on the object to be inspected may improve the inspection accuracy.

As used herein and in the appended claims, the singular form of a word includes the plural, and vice versa, unless the context clearly dictates otherwise. Thus, the references "a", "an", and "the" are generally inclusive of the plurals of the respective terms. Similarly, the words "comprise", "include" and grammatical variations are to be interpreted inclusively rather than exclusively, unless such a construction is clearly prohibited from the context. Where used herein the term "examples" particularly when followed by a listing of terms is merely exemplary and illustrative, and should not be deemed to be exclusive or comprehensive.

The foregoing description of the embodiment has been provided for purpose of illustration and description. It is not intended to be exhaustive or to limit the application. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the application, and all such modifications are included within the scope of the application.

What is claimed is:

1. A method for determining an illumination intensity for inspection, the method comprising:

acquiring images of different regions of a sample to be inspected taken by each of a plurality of imaging elements at a plurality of illumination intensities;

calculating, for each imaging element of the plurality of imaging elements, a gray standard deviation of each of the images acquired at the plurality of illumination intensities; and determining the illumination intensity of said each imaging element for inspection according to the gray standard deviation of said each of the images acquired at the plurality of illumination intensities, wherein determining the illumination intensity of said each imaging element includes normalizing the gray standard deviations for said each imaging element, determining a preferred illumination intensity range of said each imaging element according to the normalized gray standard deviations and a corresponding relationship between the normalized gray standard deviations and the plurality of illumination intensities, acquiring an intersection of the preferred illumination intensity ranges of the plurality of imaging elements, and determining the illumination intensity of said each imaging element for inspection according to the intersection.

2. The method according to claim 1, wherein determining the preferred illumination intensity range of said each imaging element comprises:
determining a range between the illumination intensities corresponding to the normalized gray standard deviations that is equal to a predetermined value as the preferred illumination intensity range of said each imaging element.

3. The method according to claim 2, wherein acquiring the intersection of the preferred illumination intensity ranges of the plurality of imaging elements comprises:
determining whether there is the intersection among the preferred illumination intensity ranges of the individual imaging elements, and if so, acquiring the intersection;
otherwise, gradually reducing the predetermined value until there is the intersection among the acquired preferred illumination intensity ranges of the individual imaging elements and acquiring the intersection.

4. The method according to claim 3, wherein the predetermined value is no less than 0.8.

5. The method according to claim 2, wherein determining the illumination intensity of said each imaging element for inspection according to the intersection comprises:
determining an intermediate value in the intersection as the illumination intensity of said each imaging element for inspection.

6. The method according to claim 1, wherein determining the illumination intensity of said each imaging element for inspection according to the intersection comprises:
determining an intermediate value in the intersection as the illumination intensity of said each imaging element for inspection.

7. The method according to claim 1, wherein the sample to be inspected is a color film substrate, a thin film transistor array substrate, or a printed circuit board for a liquid crystal display.

8. An method for optical inspection, comprising:
selecting at least one object to be inspected from a plurality of objects to be inspected as a sample to be inspected;
determining the illumination intensity of said each imaging element for inspection according to the method of claim 1, by using the sample to be inspected; and
optically inspecting the plurality of objects to be inspected by using the determined illumination intensity of said each imaging element.

9. An apparatus for determining an illumination intensity for inspection, the apparatus comprising:
a plurality of imaging elements configured to take images of different regions of a sample to be inspected; and
a processor configured to acquire images of the sample to be inspected taken by each imaging element of the plurality of imaging elements at a plurality of illumination intensities, calculate, for said each imaging element, a gray standard deviation of each of the images acquired at the plurality of illumination intensities, normalize the gray standard deviations for said each imaging element, determine a preferred illumination intensity range of said each imaging element according to the normalized gray standard deviations and a corresponding relationship between the normalized gray standard deviations and the plurality of illumination intensities, acquire an intersection of the preferred illumination intensity ranges of the plurality of imaging elements, and determine the illumination intensity of said each imaging element acquired at the plurality of illumination intensities for inspection according to the intersection.

10. The apparatus according to claim 9, wherein the processor is further configured to:
determine a range between the illumination intensities corresponding to the normalized gray standard deviations that is equal to a predetermined value as the preferred illumination intensity range of said each imaging element.

11. The apparatus according to claim 10, wherein the processor is further configured to:
determine whether there is the intersection among the preferred illumination intensity ranges of the individual imaging elements, and if so, acquire the intersection among the preferred illumination intensity ranges of the plurality of imaging elements;
otherwise, gradually reduce the predetermined value until there is the intersection among the acquired preferred illumination intensity ranges of the individual imaging elements.

12. The apparatus according to claim 11, wherein the predetermined value is no less than 0.8.

13. The apparatus according to claim 9, wherein the processor is further configured to:
determine an intermediate value in the intersection as the illumination intensity of said each imaging element for inspection.

14. An optical inspection apparatus comprising the apparatus of claim 9.

* * * * *